United States Patent

Mahoney et al.

[11] Patent Number: 5,874,100
[45] Date of Patent: Feb. 23, 1999

[54] ALGINATE FIBRES, MANUFACTURE AND USE

[75] Inventors: Peter M. J. Mahoney, Powys; K. Walker, Farnham, both of Great Britain

[73] Assignee: Bristol-Myers Squibb Company, New York, N.Y.

[21] Appl. No.: 765,569
[22] PCT Filed: Jul. 14, 1995
[86] PCT No.: PCT/EP95/02772
  § 371 Date: Jul. 7, 1997
  § 102(e) Date: Jul. 7, 1997
[87] PCT Pub. No.: WO96/02285
  PCT Pub. Date: Feb. 1, 1996

[30] Foreign Application Priority Data

Jul. 15, 1994 [GB] United Kingdom .................. 9414304

[51] Int. Cl.⁶ ........................................................ A61F 2/02
[52] U.S. Cl. .......................................... 424/426; 514/779
[58] Field of Search .............................. 424/426; 514/779

[56] References Cited

U.S. PATENT DOCUMENTS 5,578,314 11/1996 Cochrum et al. ...................... 424/424

FOREIGN PATENT DOCUMENTS

| 9001954 | 3/1990 | WIPO . |
| 9107951 | 6/1991 | WIPO . |
| 9303710 | 3/1993 | WIPO . |
| 9316111 | 8/1993 | WIPO . |
| 9400164 | 1/1994 | WIPO . |
| 9417227 | 8/1994 | WIPO . |

*Primary Examiner*—Carlos A. Azpuru
*Attorney, Agent, or Firm*—John M. Kilcoyne; Theodore R. Furman, Jr.

[57] ABSTRACT

A non-immunogenic, bioerodible implantation composition which comprises alginate fibres.

12 Claims, 6 Drawing Sheets

FIG. 1 TGA

ALGINATE FIBRES, MANUFACTURE AND USE

BACKGROUND OF THE INVENTION

The present invention relates to alginate fibres and a process for their preparation and their use. In particular the present invention relates to an implantation composition comprising alginate fibres.

A number of methods for producing conventional alginate fibres are described in the art. The extrusion of alginate solutions into an aqueous solution containing calcium ions to form calcium alginate filaments is known, for example, from British Patent Specifications Nos. 567641, 568177, 571657 and 624987. The replacement of a proportion of the calcium ions in calcium alginate by sodium ions to produce a more soluble fibre is known from British Patent Specification No. 653341.

Alginate is a heterogeneous group of linear binary copolymers of 1–4 linked β-D-mannuronic acid (M) and its C-5 epimer Ó-L-guluronic acid (G). The monomers are arranged in a blockwise pattern along the polymeric chain where homopolymeric regions (M blocks and G blocks) are interspaced with sequences containing both monomers (MG blocks). The proportion and sequential arrangement of the uronic acids in alginate depend upon the species of algae and the kind of algal tissue from which the material is prepared.

Commercial alginates are produced mainly from *Laminaria hyperborea, Macrocystis pyrifera, Laminaria digitata, Ascophyllum nodosum, Laminaria japonica, Eclonia maxima, Lesonia negrescens* and *Saragassum sp.*

Alginate fibres have been known for some time as being useful in the preparation of wound dressings. For example, EP 433354 describes a wound dressing comprising a backing layer and a wound contact pad, the latter comprising a mixed salt alginate. EP 476756 describes a non-woven alginate fabric useful for the preparation of wound and burn dressings, the fabric being characterised in terms of its absorptive properties whereby the absorbency of the fabric is greater than 25.0 grams of deionised water or 19.0 grams of saline water per gram of fabric.

Alginates have also been used in transplantation and implantation compositions, however this use of alginates has been somewhat problematic due to immunogenic responses which have been observed. For example, Lim and Sun ((1980) Science 210, 908) microencapsulated islets using alginate gel, poly-L-lysine and polyethylenimine. The encapsulated islets were injected intraperitoneally into diabetic rats. The animals' blood glucose levels dropped to normal for two to three weeks, suggesting that the encapsulation process had protected the islets from invasion by the recipients' immune system. However, these studies showed that the microcapsules were eventually rejected as a result of fibrosis, or fibroblast formulation around the microcapsule, which eventually restricts the flow of nutrients to the cells contained in the microcapsule and the outflow of material from the microcapsule created by the islet cells disposed therein.

WO91/07951 describes a transplantation or implantation composition which provokes a reduced immune response and which employs an alginate comprising greater than 50% L-guluronic acid. The compositions described by WO91/07951 would not however be bioerodible when incorporated within the body cavity.

DETAILED DESCRIPTION OF THE INVENTION

Alginate fibres which alleviate the above problems have now been discovered, and there is provided by the present invention a non-immunogenic, bioerodible implantation composition which comprises alginate fibres.

Implantation compositions according to the present invention are seen to induce substantially no immune response when implanted in a mammalian body for a residence time of up to 4 to 6 months. Accordingly, it is generally preferred that the alginate fibres employed in compositions according to the present invention have a mid or high guluronic acid content, by which is meant the fibres comprise 50 to 80% by weight guluronic acid.

Compositions according to the present invention are 'bioerodible', as hereinbefore described, in that when present in a mammalian body they are seen to be degradable in situ leaving substantially no detectable alginate fibre within the body. For example, infra red analysis was seen to find no detectable alginate fibre (mixed salt) employed according to the invention present in an implant site in liver tissue, at 28 days after implantation.

Typical erosion times of compositions according to the present invention will vary from about one week up to several months, such as four to six months, dependent, inter alia, on the nature of the alginate salt employed. Increased amounts of insolubilising ions will increase the erosion times of the compositions, whereas conversely increased amount of solubilising ions will decrease the erosion times.

In the case where a solubilising ion is employed a typical erosion time in a mammalian body will be of the order of about 1 to 3 weeks. Suitable solubilising ions include sodium, potassium, lithium, ammonium, magnesium and the like, sodium being preferred. In the case where the alginate salt employs an insolubilising ion such as calcium, zinc and the like, typically calcium, an erosion time in a mammalian body will be of the order of several months such as 3 to 5 months, or even up to 6 months. In the case of a mixed salt alginate employing a solubilising and an insolubilising ion, such as sodium and calcium, typical erosion times of compositions according to the present invention will be of the order of 3 weeks to 2 months. The above erosion times will further be dependent on other factors, such as, for example, the rate of metabolic activity at the implant site.

Aptly the alginate fibres according to the present invention comprise a mixed salt alginate which has first and second cations, the first cation being capable of forming an insoluble alginate salt and the second cation being capable of forming a soluble alginate salt. Suitably the first cation is calcium, although it will be appreciated that other cations such as zinc and the like could be employed. Typically the second cation comprises a solubilising cation such as sodium, potassium, litium, ammonium, magnesium and the like, sodium being preferred.

Apt ratios of the first (insolubilising) to the second (solubilising) cations is in the range of 20:80% to 100:0% by weight.

The bioerosion characteristics of alginate fibres employed in the implantation compositions of the present invention can therefore be tailored depending on the required application of the compositions. Skilled researchers will appreciate that it is extremely advantageous to be able to select the erosion characteristics of the implantation compositions in this way.

Exemplary applications of compositions according to the present invention include bioerodible sutures; bioerodible support structures used in surgical applications, such as surgical nets used in organ support conventionally during spleen, liver or kidney repair or the like; bioerodible drug delivery systems, exemplary drugs being substantially as hereinafter described; use in sinus cavities for example in obviating the trapping of bacteria in such cavities as a result of closure of the latter from the outside; for use as internal haemostatic swabs and the like.

Typically the sutures comprise alginate fibres, aptly provided in rope form, suitably of 2.5 to 3.5 mm in diameter and of 2.5 to 3.5 cm in length. Aptly the alginate fibre employed in the sutures comprise a solubilising ion, or both solubilising and insolubilising ions. Such sutures will typically erode over a period of 6 to 10 days when the algiante fibres employ a solubilising ion, such as sodium, or over a period of 4 to 6 weeks when a mixed salt alginate, such as a sodium/calcium alginate is employed.

In the case of surgical support nets, these may be employed during surgery to facilitate operation on the body by a surgeon. Alternatively, or in addition thereto, surgical supports prepared from an implantation composition according to the present invention can be retained in the body following surgery in view of the non-immunogenic and bioerodible properties thereof. In the latter application the use of these supports is desirable in supporting organs during recovery following surgery. Suitably the nets employ alginate fibres, aptly in rope form, typically of 2.5 to 3.5 mm in diameter, and 2.5 to 3.5 cm in length as described above, and exhibit erosion characteristics as described with reference to the sutures.

The drug delivery system may be in pad or sliver form. Suitably the dimension and erosion characteristics of a drug delivery system in the form of a pad are as hereinafter described with reference to the internal haemostatic swabs. The sliver is typically of 3 to 5 mm in diameter and 10 to 20 cm in length and typically erode over a time period of 1 to 2 weeks, 5 to 7 weeks and three to four months in respective cases where solubilising, solubilising/insolubilising and insolubilising ions are employed.

Aptly the drug delivery system includes an antibiotic, such as gentamycin sulphate, and in an advantageous application of the present invention the delivery system, in the form of a pad or sliver, is employed at a site of infection, often in a case where part of a patient's bone has been removed. A further advantageous application of the present invention is in dental treatment, wherein aptly a sliver of alginate fibre as hereinbefore described is administered to a treatment site in a patient's mouth. In this latter application a preferred medicament comprises an antiprotozoal agent such as metronidazole.

Suitably slivers of alginate fibres are employed in the treatment of sinus cavities, suitably of 3 to 5 mm in diameter and 10 to 20 cm in length and exhibit erosion characteristics as described above with reference to the slivers for use as drug delivery systems.

Suitably pads of alginate fibres are employed as internal haemostatic swabs, the size and shape thereof being adapted for their intended use, aptly the swabs can be 0.5 to 7.5 mm thick and are preferably 1 to 5 mm thick, for example 1.5 to 3 mm thick. Typical swab sizes are rectangular with sides of from 4 to 20 cm, for example 5 to 15 cm, 10 to 10 cm and the like although other shapes may be employed such as circular, oval or the like. Typically the pad is a wet-laid pad of fibres which if desired can be needle-tacked or hydraulically entangled. The swabs typically have erosion times within the range of 2 to 3 weeks, 6 to 8 weeks and three to five months in the respective cases when solubilising, solubilising/insolubilising and insolubilising ions are employed.

According to an alternative aspect of the present invention there is provided alginate fibres for use as a non-immunogenic, bioerodible implantation composition substantially as hereinbefore described, and further a method of treating a mammalian animal, which method comprises implanting non-immunogenic bioerodible alginate fibres in a mammalian body. The nature of the fibres and the site of the implant will be dependent on the treatment required.

The fibres employed in a composition according to the invention may be characterised by reference to their unique thermal properties, in that a plot of the first order derivative of percentage weight loss of the fibre with temperature against temperature has two maxima in the range of 100° to 400° C.

In general, the two maxima in the plot of the first order derivative of percentage weight loss with temperature against temperature for a fibre according to the invention will fall within the range 200° to 300° C., preferably 220° to 290° C.

Figure 1:
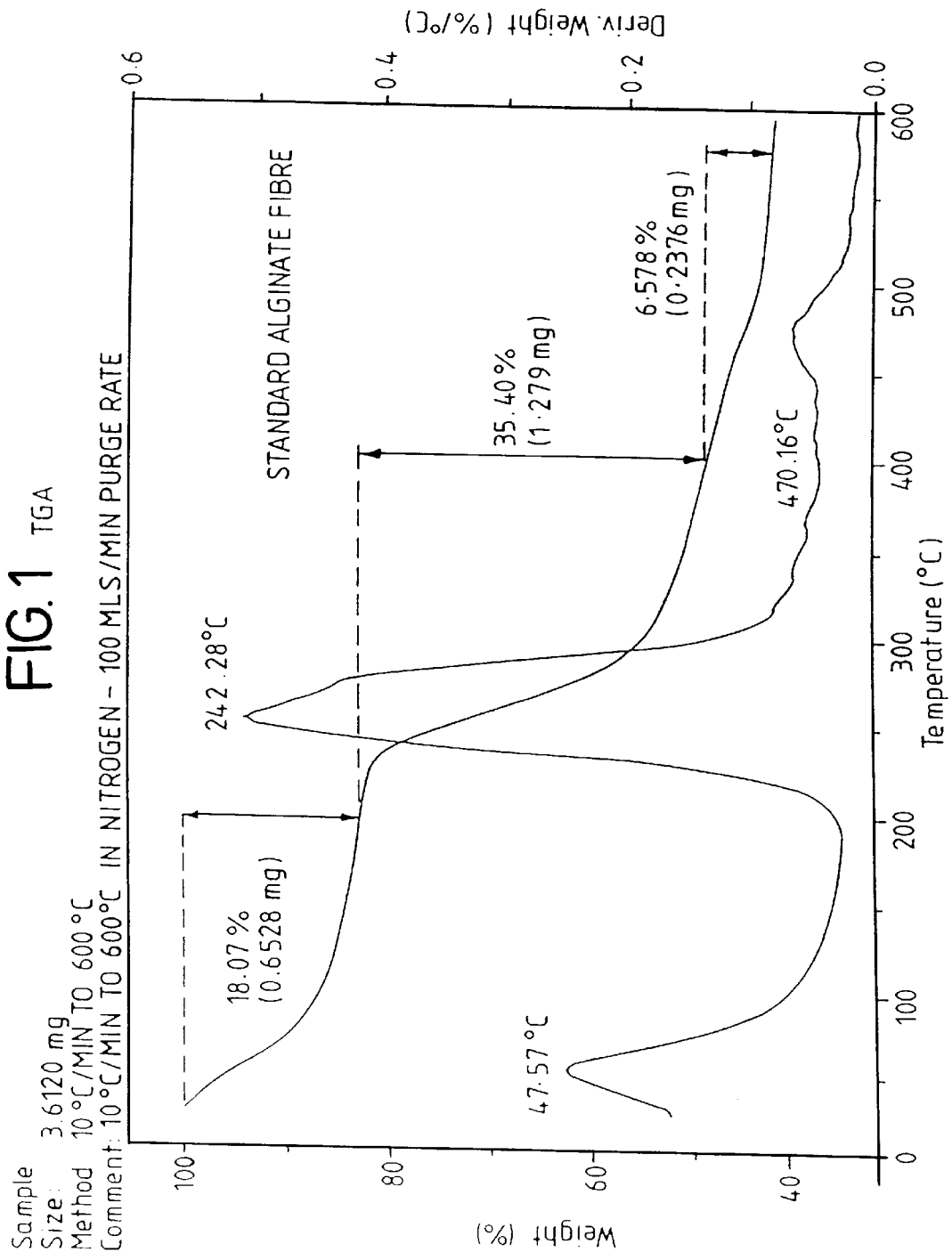
FIG. 1 shows the thermogravimetric analysis (TGA) of an 80:20 calcium:sodium alginate fibre prepared by conventional methods.
Figure 2:
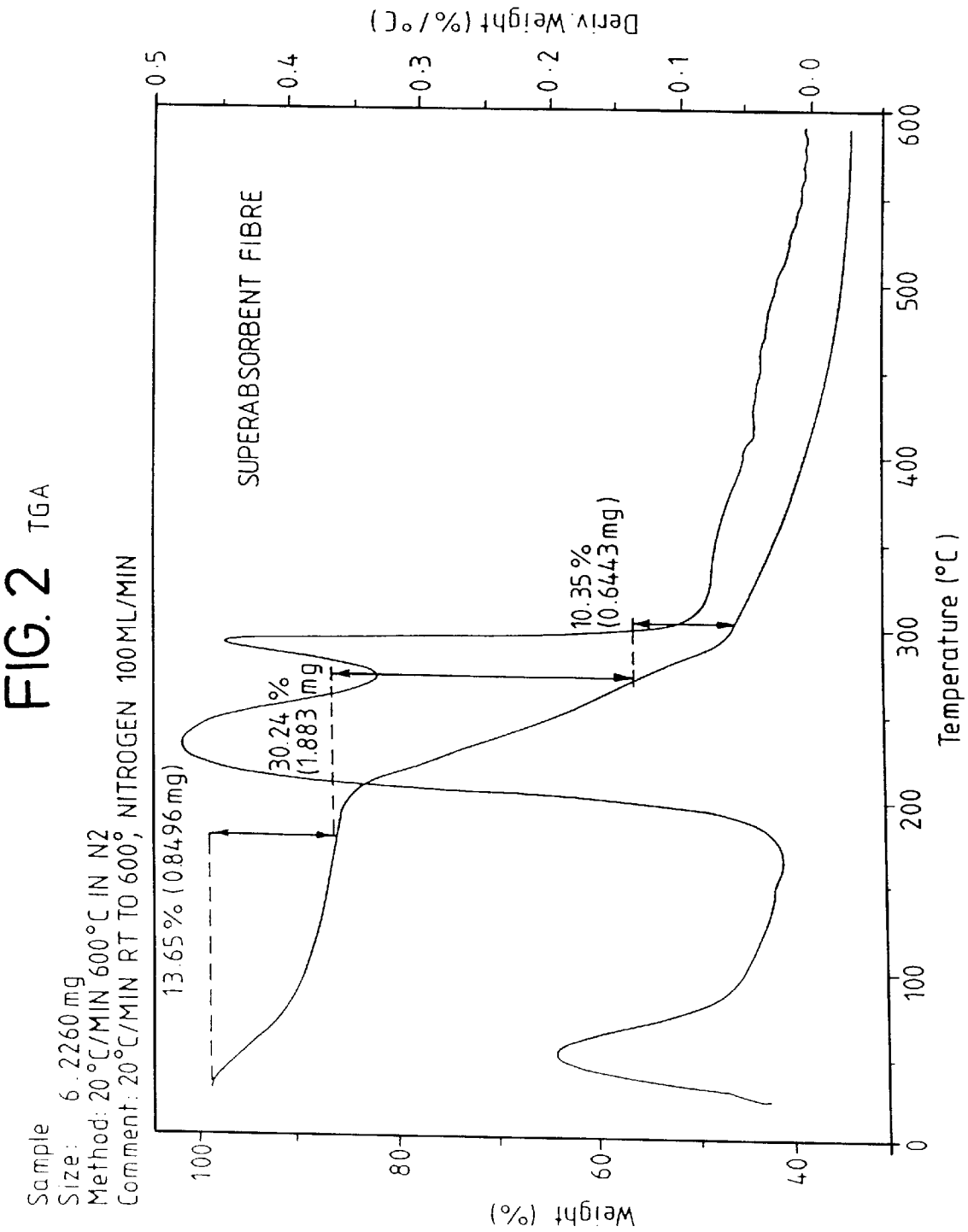
FIG. 2 shows the thermogravimetric analysis (TGA) of a fibre employed in a composition according to the invention, prepared from the same source material as the fibre of FIG. 1.

FIG. 1 shows the percentage weight loss of a conventional alginate fibre with increasing temperature, and the first order derivative of that function. The derivative shows a single maximum at approximately 240° C. In contrast, the first order derivative of percentage weight loss with temperature for a corresponding fibre employed in a composition according to the present invention, shown in FIG. 2, has two peaks, one at a lower temperature than the maximum observed for the conventional fibre (approximately 225° C.), and one at a higher temperature than the maximum observed for the conventional fibre (approximately 280° C.). This "splitting" of the derivative maximum for the conventional fibre of the same composition is characteristic of fibres employed according to the present invention.

Figure 3:
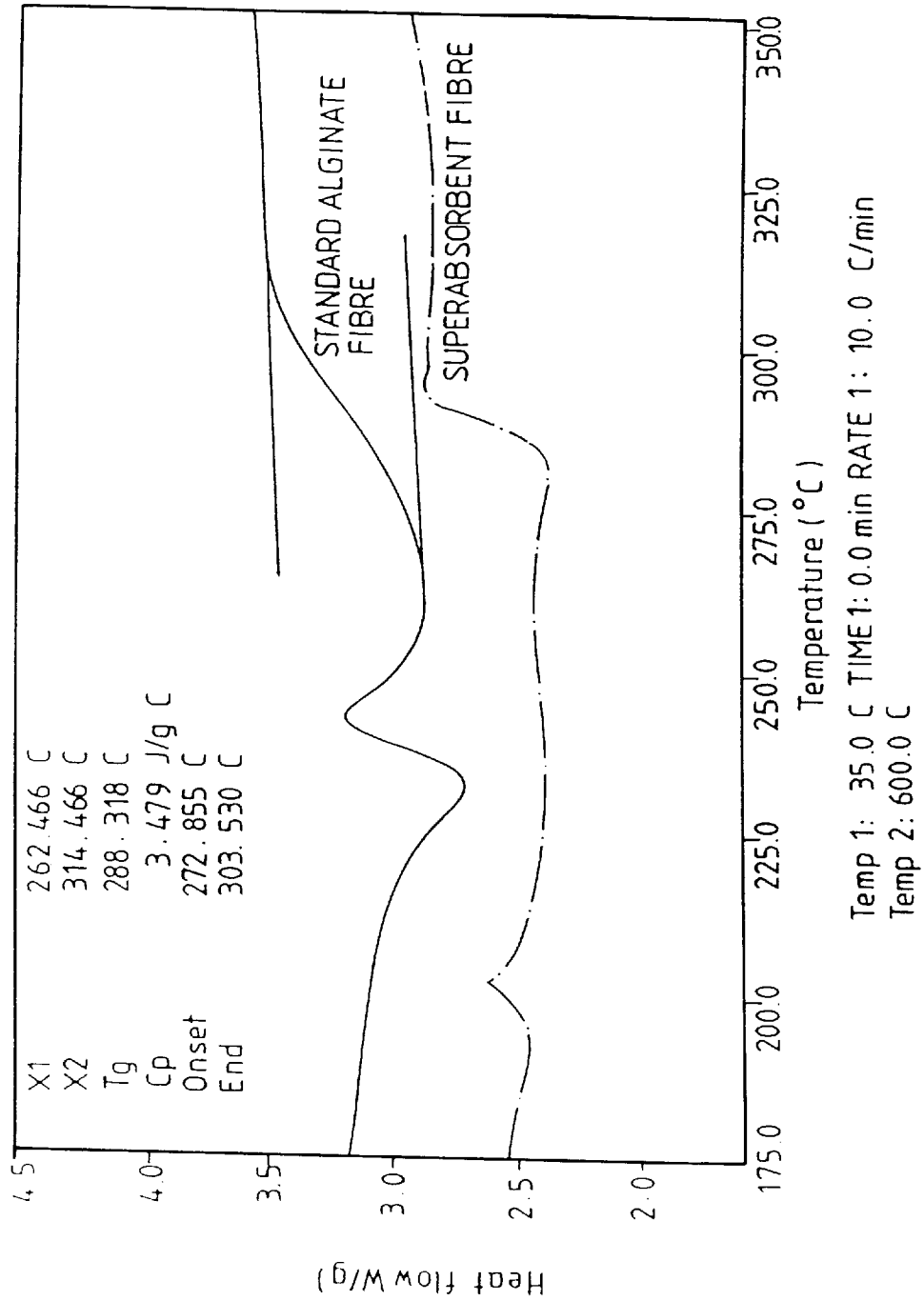
FIG. 3 shows the variation of heat flow with temperature for a conventional 80:20 calcium:sodium alginate fibre and a corresponding fibre employed in a composition in accordance with the present invention.
Figure 4:
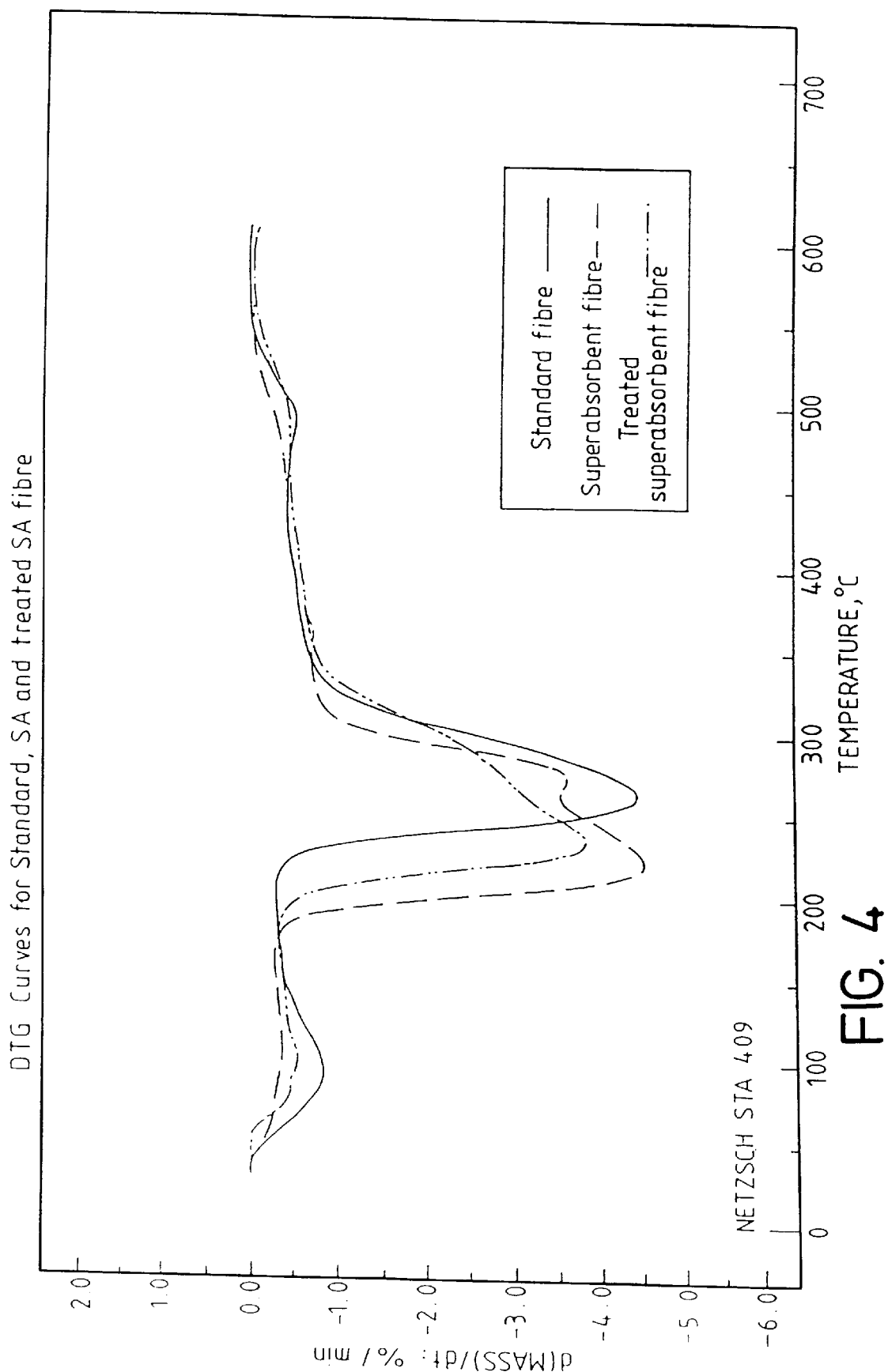
FIG. 4 shows the thermogravimetric analysis of a conventional fibre, a high absorbency fibre employed in this invention and such a fibre treated with calcium ions.

FIG. 3 also shows differences in the thermal properties of a conventional alginate fibre and a fibre employed according to the present invention. Heat flow is effectively a measure of enthalpy associated with a transition, reaction or decomposition. The glass transition termperature (Tg) shown in FIG. 3 is the same for both fibres (288° C.). However, it can be seen that the transition for the conventional fibre is broad, occuring over some 50° C., whereas that for the fibre in accordance with the invention is sharp, taking place over less than 20° C.

Alginate fibres employed in compositions according to the present invention can further be characterised in terms of their glass transition temperature, and in a further or alternative aspect, the present invention thus provides a non-immunogenic, bioerodible composition comprising alginate fibre having a glass transition temperature range of less than 30° C., such as about 26° C.

Figure 5:
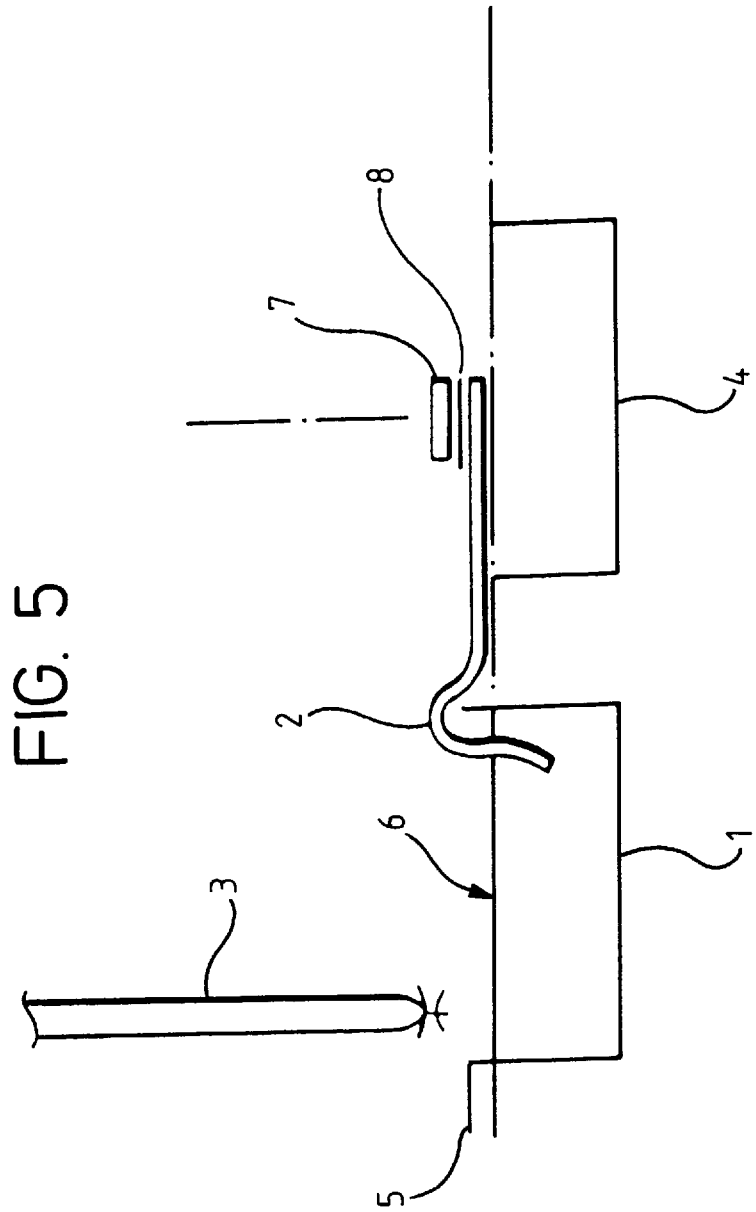
FIG. 5 shows apparatus suitable for determining absorbency.

Alginate fibres employed in compositions of the present invention exhibit improved absorptive properties and the present invention accordingly provides a non-immunogenic, bioerodible compositions comprising alginate fibres wherein the absorbency of the fibres may be at least 40.0 grams of deionised water per gram of fibres as measured with reference to a test method depicted in FIG. 5 appended hereto.

Alginate fibres employed in the present invention aptly have an absorbency of at least 40 times their own weight of deionised water and more aptly at least 60 times and most aptly at least 80 times its own weight of deionised water. Typically the fibres have an absorbency of much greater than this, for example 80 to 280 times their own weight, such as about 120 grams of deionised water per gram of fibres.

Compositions according to the present invention may have medicaments incorporated therein. Suitable medicaments for use in conjunction with the alginate fibre according to the invention include antibacterial agents, for example bisbiguanide derivatives such as chlorhexidine, both in the free base form and as the acetate, gluconate or hydrochloride salts, tetracycline derivatives such as chlorotetracycline; nisin, a polypeptide available in nature from various strains of the bacterium streptococcus lactis; oxytetracycline and tetracycline itself, and sulphonamide derivatives such as sulphadiazine; antiprotozoal agents, for example imidazole derivatives such as metronidazole; antifungal agents such as chlorphenesin; phenothiazine derivatives such as promethazine and chlorpromazine; nucleosides such as iodouridine; hormones such as noradrenalin, insulin, growth hormones, secretin, vasopressin, substance P and the like; antibiotics, such as gentamycin sulphate and the like; antiinflammatory agents, for example steroid derivatives such as hydrocortisone and prednisolone; angiogenisis promoting agents and the like. Compositions incorporating medicaments are prepared by treating the fibres with an aqueous solution of the medicament or its salt.

It has further been found that hyaluronic acid can be incorporated into the alginate fibres of the compositions according to the present invention.

Hyaluronic acid (hereinafter referred to as HA) is a natural high viscosity mucopolysaccharide, generally having a molecular weight range of $3 \times 10^3$ to $8 \times 10^6$ Daltons (although there are reports of HA having molecular weights as high as $13 \times 10^6$) depending on source, method of isolation and method of determination. The isolation and characterisation of HA are described in Meyer, et al., J. Biol. Chem. 107, 629, (1934); J. Biol. Chem. 114, 689, (1936); Balazs, Fed. Proc. 17, 1086, (1958); Laurent, et al., Biochem. Biophys. Acta. 42, 476, (1960); Weissman, et al., J. Am. Chem. Soc., 76, 1753, (1954); and Meyer, Fed. Proc. 17, 1075, (1958).

HA is normally employed as its sodium salt although some other salting ions such as potassium or calcium or the like may also be present. All such physiologically acceptable forms and especially the sodium salt are encompassed within the term HA herein.

HA is frequently used in ocular surgery as a replacement for subretinal fluid and vitreous humor. HA can also be used as a replacement for synovial fluid that is lost as a result of surgery or chronic inflammatory disease such as rheumatoid arthritis. HA is also known to be implicated in wound healing and angiogenesis. A wound dressing capable of providing sustained release of hyaluronic acid might therefore be expected to promote wound healing and/or angiogenesis.

A suitable average molecular weight range for HA for use in the fibres employed in the present invention is $1.5 \times 10^3$ to $2 \times 10^6$, such as $1 \times 10^4$ to $1 \times 10^6$, preferably $1.5 \times 10^4$ to $1 \times 10^5$, more preferably about $7.5 \times 10^4$.

It is believed that the HA incorporated into alginate fibres of the compositions of the invention resides in spaces or "pockets" in the internal structure of the fibre and that release of the HA from the fibre to the environment of use takes place in a sustained manner as the fibre swells under the conditions of use.

Incorporation of HA into the alginate fibres may be achieved by contacting alginate fibres with an aqueous solution of HA followed by a suitable aqueous ionic solution, such as a solution of calcium, magnesium or zinc cations, preferably a solution of calcium cations, more preferably aqueous calcium chloride solution.

Alginate fibres suitable for preparing a composition according to the present invention, are typically obtained by a process comprising the following steps:

(1) treating alginate fibres with a suitable acid so as to produce fibres comprising approximately 90–98%, such as 95%–98%, alginic acid fibres;

(2) treating the alginic acid fibres with a saturated aqueous solution of mono- or divalent cations;

(3) washing the fibres with water until imbibition of water by the fibres has effectively ceased;

(4) treating the fibres with a source of a cation capable of forming a water-soluble alginate salt.

The present invention also provides a non-immunogenic, bioerodible implantation composition comprising alginate fibres prepared according to the abovedescribed process.

The fibres used as starting material in step 1 may be conventional salted alginate fibres (for example sodium, calcium, mixed sodium/calcium fibres produced in conventional manner, for example from 2–10% w/w solutions, for example 4% solution).

Most suitably the alginate fibres for use in step (1) are calcium alginate fibres, which can be spun from a dope solution of 2 to 8% by weight sodium alginate, suitably 4 to 6% by weight, employing techniques conventional to the art.

As hereinbefore described, the alginate fibres preferably have a mid or high guluronic acid content, and aptly the fibres employed as starting materials are produced by *Laminaria hyperborea* or *Eclonia maxima*.

Suitable acids for use in step (1) include acids capable of protonating alginic acid and may include both organic and inorganic acids. Preferably, hydrochloric acid will be used. Preferably the resulting alginic acid fibres have at least 95% of the acid residues in the unsalted form.

Suitable mono- or divalent cations for use in step (2) include solutions of sodium, potassium and magnesium cations. Preferably a pharmaceutically acceptable monovalent cation is used, most preferably a sodium ion.

Step (3) is preferably effected by washing the fibres in a stream of deionised water. Desirably step (3) may be discontinued when swelling has ceased.

Cations capable of forming water-soluble alginate salts include, for example, sodium, potassium, lithium, ammonium and magnesium cations. Preferably the source of a cation capable of forming a water-soluble alginate salt used in step (4) is a source of sodium cations, more preferably sodium carbonate. Other carbonates may be used in like manner to produce the alternative salts.

Small quantities of other ions (for example zinc or silver) may be present in step (4) if desired but generally these may be included in the fibre after completion of step (4) if their presence is required.

A method of treating the product of the above process to include other ions is to treat the product with an aqueous solution of a source of the ions.

The fibres may be collected at the end of step (4) by filtration or other suitable method and may be dried, for example by treatment with a volatile drying agent, such as methyl alcohol, ethyl alcohol, isopropyl alcohol, acetone and the like, and then drying in air. It is one of the advantages of this invention that the highly absorbent fibres may be dried without losing their ability to be highly absorbent when rewetted.

For the most highly absorbent products to be obtained, large amounts of divalent ions such as calcium ions are not added at step (4) or later.

The solubility of the fibres may be modified by choosing the degree of neutralisation of the unsalted carbonyl groups by solubilizing ion. Thus for example, if a sheet of fibres (such as may be employed in a dressing) is required which is highly absorbent but which will remain intact as gelled fibres, the fibres are produced under conditions where a small proportion of residual carboxy groups is retained (for example by using insufficient $Na_2CO_3$ or the like to effect complete neutralisation). Alternatively, the material can be made fully soluble by replacing essentially all of the unsalted carboxy groups with a solubilizing ion such as sodium (for example by using at least a sufficient amount of $Na_2CO_3$ or the like to effect complete neutralisation).

A method of preparing fibres having a higher content of insolubilising cations, such as calcium, than those prepared directly by the process described above which employs sufficient $Na_2CO_3$ is to treat the fibre with insolubilising ions, such as calcium ions, for example from a solution of calcium chloride, calcium sulphate, or the like, so that some of the sodium ions are replaced by calcium ions. Suitably calcium chloride is employed.

The absorbency of fibres employed in compositions according to the invention may be determined according to the following method.

TEST METHOD

The apparatus used in the determination of absorbency is depicted in FIG. 5, and consists of water bath 1 containing a 0.9% (w/w) aqueous saline solution, or deionised water, absorbent strip 2, burette 3, top-pan balance 4 and overflow 5.

The thickness of the absorbent strip 2 is substantially equivalent to that of the dressing 7. The filter paper 8 has substantially the same planar dimensions as the dressing 7, but not necessarily the same thickness.

The apparatus is set up with the surface 6 of the saline solution or water level with the top surface of the top-pan balance 4. The flow of liquid from the burette 3 is then adjusted to approximately 1.5 ml per minute. The absorbent strip 2 is then saturated and placed between the bath 1 and the balance 4, as depicted in FIG. 5. The balance 4 is then tared. A weighed dressing 7 and filter paper 8 (cut to size) is positioned is as depicted in FIG. 5. Care must be taken to ensure that the edge of the absorbent strip 2 furthest away from the water bath 1 does not extend beyond the corresponding edge of the dressing 7, as shown in FIG. 5.

After six minutes the weight shown on the balance 4 is recorded. The dressing 7 and filter paper 8 are then removed and any residual weight on the balance 4 noted.

Absorbency is determined on the basis of the following equation:

| Weight of liquid absorbed | = | total weight on balance | − | dry weight of dressing | + | weight of saturated filter paper | + | residual weight on balance |
|---|---|---|---|---|---|---|---|---|

TEST METHOD 2

The Tanδ value of a fibre was determined by using a Thurlby Thandor TG502 sweep/function generator, a Tectronics 2212 digital storage oscilloscope and a capacitance test cell (plate area 16 square centimeters and fitted with a 22KΩ resistor). The material to be tested was placed in a small engineers vice and the vice closed. The distance between the plates was measured using a vernier calliper and the earth connection made between the vice and the earth terminal of the capacitance test cell. The function generator and oscilloscope were then connected and the amplitude of the applied sinusoidal voltage measured together with the voltage drop across the resistor and the phase angle between the applied voltage signal and current. The frequency of the applied field was then altered and the measurements repeated for many points in the range 5 mHz to 5 MHZ.

The following non-limiting Examples are intended to illustrate the present invention.

EXAMPLE 1

Calcium alginate fibres were spun form a dope solution containing 4 to 6% sodium alginate employing conventional techniques, and 4 g of the resultant alginate fibres were immersed in 1M hydrochloric acid (1 liter) for 20–30 seconds. The degree of acid conversion was determined from the relative intensities of the peaks at 1720 $cm^{-1}$ and 1600 $cm^{-1}$ in the infrared spectrum, to ensure that the degree of conversion was in excess of 95%. The fibre was then washed with water and immersed in saturated saline solution (2 liters). The fibre was then chopped to the required staple length (2.5 to 3.5 cm). After cutting to the appropriate length the fibre was dispersed into a stirring vessel containing deionised water (2 liters). The fibres were washed in a stream of running water until they swelled to their maximum extent and no sodium chloride could be deteced in the eluent. Sodium carbonate solution (0.1M) was then added in 1 ml aliquots whilst monitoring the pH and the conductivity of the medium. Care was taken to ensure that the pH did not exceed 6.5. After the addition of approximately 12 mls of sodium carbonate solution (conductivity meter reading between 180 and 200 micro siemens), the material was filtered and dried with acetone followed by air drying.

The product was then re-suspended in water (200 $cm^3$) and filtered through a Buchner funnel. Three aliquots (50 $cm^3$) of calcium chloride solution (0.1M) were then slowly filtered through the pad followed by washing with water (200 $cm^3$). The pad was removed and the calcium/sodium content determined by atomic absorption spectrometry (99% calcium, 1% sodium). The pad was then air dried at room temperature.

The resultant pad was suitable for use in an implantation composition, such as a haemostatic swab, according to the present invention.

EXAMPLE 2

Figure 6:
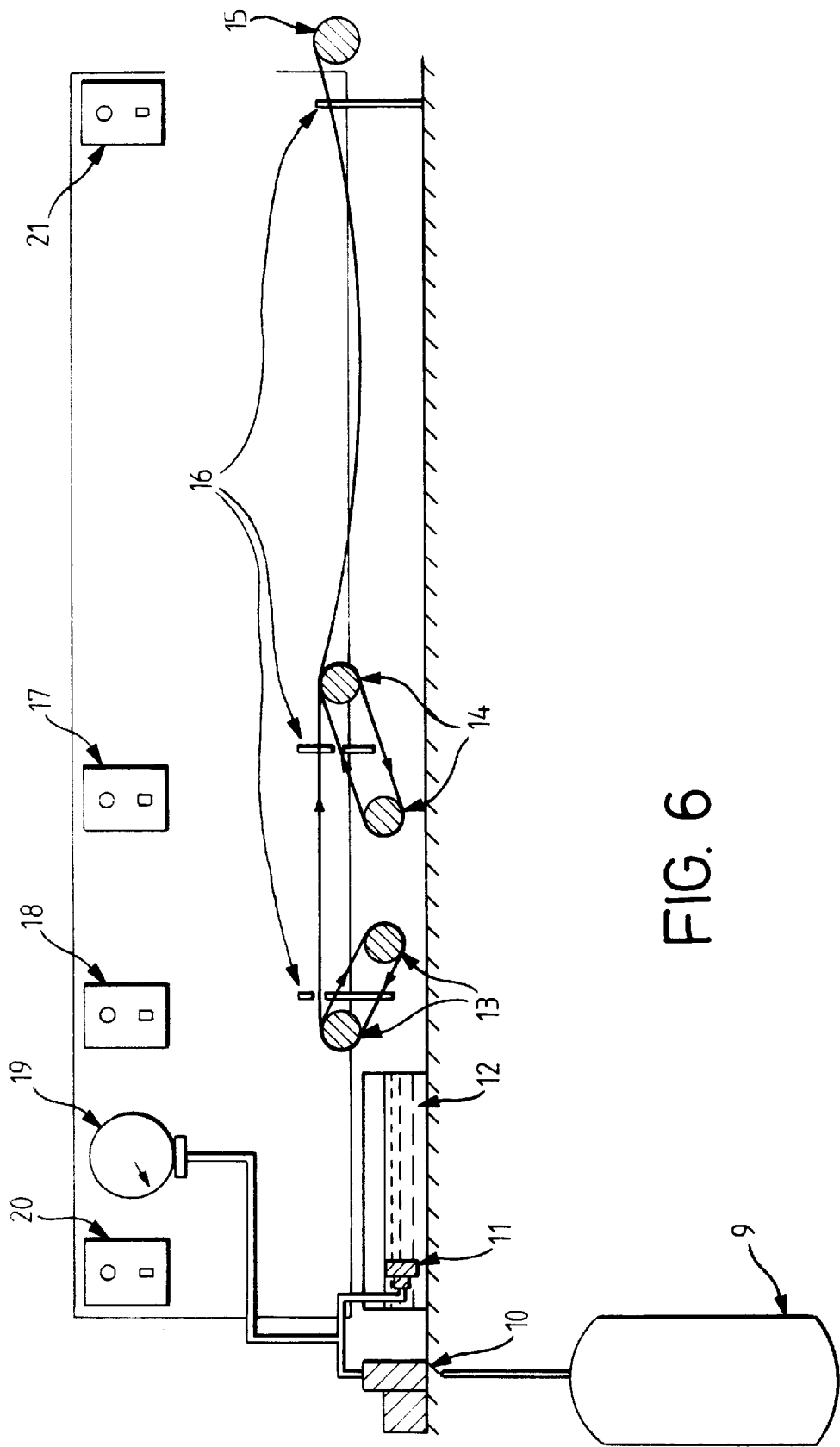
FIG. 6 shows apparatus for the preparation of alginate fibres suitable for use as biodegradable sutures Thermogravimetric analysis was performed using a 2950TGA manufactured by TA Instruments, Delaware, U.S.A. Differential scanning calorimetry (DSC) was performed using a DSC7 manufactured by Perkin-Elmer.

This example describes the preparation of alginate fibre suitable for use as biodegradable sutures, and employs the apparatus depicted in FIG. 6.

Referring to FIG. 6, the apparatus comprises a dope reservoir 9 connected to a pump 10 which effects transfer of a dope solution from reservoir 9 to a spinnerette 11 for extrusion into spin bath 12. For control of the transfer of dope solution, a pump controller 20 and spinnerette pressure gauge 19 are provided.

Godets 13, 14, provided with control systems 17, 18, effect stretching of fibre prior to collection thereof by a wind up roller 15 provided with a control system 21. Guides 16 are provided to control passage of fibre around godets 13, 14.

Sodium alginate (25 g) was dissolved in water (500 $cm^3$). The solution was allowed to stand for 24 hours and then added to the pressured dope reservoir 9 shown in FIG. 6. The solution was then extruded through the spinnerette (5000 hole 75 μm) at a rate of 120 $cm^3$ per minute into spin bath 12 containing 10 liters of calcium chloride solution (0.2M).

The yarn was stretched to between 150% and 170% and collected on the wind up roller 15.

The yarn and its wind up roller 15 were then immersed in 1M HCl for 2 minutes and transferred to a bath containing a saturated solution of sodium chloride (2 liters). After 10 minutes the yarn and holder were washed exhaustively under running water until no sodium chloride could be detected in the eluent.

The yarn and holder were then immersed in a bath of deionised water (2 liters). Sodium carbonate solution (0.1M, 12 cm$^3$) was then added slowly whilst ensuring that the pH did not exceed 7.5. The product was then removed, washed in water (20 cm$^3$) and placed in a bath of calcium chloride (0.1M, 2 liters) the product was then air dried.

EXAMPLE 3

An alginate pad was prepared as described in Example 1, with the exception that the process was modified so that the resulting product contained 50% calcium by weight and 50% sodium by weight.

The pad was embedded within the hepatic lobes of rats (sacrificed) and the implants were monitored for foreign body reaction and also the bioerosion properties thereof.

No observable adverse tissue reaction was seen with the implants which dissolved within two months of implantation.

EXAMPLE 4

Tanδ values were measured according to Test Method 2 above for a range of fibre samples. The results were as follows:

| Fibre | Peak 1 Hz | Peak 2 Hz | Peak 3 Hz |
|---|---|---|---|
| KALTOSTAT[1] | 6449 | 1000 | 896 |
| KALTOGEL[2] | 578 | 416 | 46 |
| KALTOSTAT acid treated, neutralised and dried. | 2929 | 541 | 54 |
| Fibre prepared as in Example 1, the resuspension treatment omitted. | 0.056 | 0.018 | — |
| Fibre prepared as in Example 1. | 5.412 | 2.928 | 0.464 |

[1]commercially available calcium sodium alginate of high guluronate content
[2]commercially available calcium sodium alginate of high malluronate content

We claim:

1. A method of treating a mammalian animal, which method comprises implanting in a mammalian body non-immunogenic, bioerodible alginate fibres mad by a process comprising the following steps:
   i. treating alginate fibres with suitable acid so as to produce fibres comprising approximately 90 to 98% alginic acid fibres;
   ii. treating the alginic acid fibres with a saturated aqueous solution of mono- or divalent cations;
   iii. washing the fibres with water until imbibition of water by the fibres has effectively ceased; and
   iv. treating the fibres with a source of a cation capable of forming a water-soluble alginate salt.

2. A method as claimed in claim 1 wherein the alginate fibres comprise 50 to 80% by weight guluronic acid.

3. A method as claimed in claim 1 wherein the alginate fibres comprise a mixed salt alginate which has first and second cations, the first cation being capable of forming an insoluble alginate salt and the second cation being capable of forming a soluble alginate salt wherein the ratio of first (insolubilising) to the second (solubilising) cations is in the range of 20:80 to 100:0 by weight.

4. A method as claimed in claim 1 wherein the absorbency of the fibres is at least 40.0 grams of deionized water per gram of fibres.

5. A method as claimed in claim 1 wherein the method comprises alginate fibres which are characterised by having a split maxima in the range of 100° C. to 400° C. in a plot of the first order derivative of percentage weight loss of the fibre with temperature against temperature.

6. A method as claimed in claim 1 wherein the method comprises fibres which are characterised by having two maxima in the range of 220° C. to 290° C. in a plot of the first order derivative of percentage weight loss of the fibre with temperature against temperature.

7. A method according to claim 1 wherein the process comprises the additional step of:
   v. treating the fibres with a source of a cation capable of forming a water-insoluble alginate salt.

8. A composition comprising alginate fibres as claimed in claim 1 wherein the alginate fibres in step i are calcium alginate.

9. A composition as claimed in claim 1 wherein other ions and/or medicaments are included after or during step (iv).

10. A method as claimed in claim 1 wherein the fibres comprise hyaluronic acid or a pharmaceutically acceptable salt thereof.

11. A method as claimed in claim 1 wherein the fibres are characterised by having a glass transition temperature range of less than 30° C.

12. A method as claimed in claim 1 wherein the fibres are characterised by having a Tanδ value in the range from 0 to 15 Hz.

* * * * *

UNITED STATES PATENT AND TRADEMARK OFFICE
CERTIFICATE OF CORRECTION

PATENT NO.   :   5,874,100
DATED        :   Feb. 23, 1999
INVENTOR(S)  :   Peter M.J. Mahoney; K. Walker It is certified that error appears in the above-identified patent and that said Letters Patent is hereby corrected as shown below:

Claim 1, line 3, change "mad" to --made--;

Claim 8, line 1, change "composition comprising alginate fibres" to --method--; and Claim 9, line 1, change "composition" to --method--.

Signed and Sealed this

Thirteenth Day of July, 1999

Attest:

Q. TODD DICKINSON

*Attesting Officer*                  *Acting Commissioner of Patents and Trademarks*